US006218350B1

(12) United States Patent
Beggs et al.

(10) Patent No.: US 6,218,350 B1
(45) Date of Patent: Apr. 17, 2001

(54) BLEACHING ENZYMES

(75) Inventors: Thomas Stewart Beggs; Mark John Berry; Paul James Davis, all of Sharnbrook (GB); Leon Gerardus J. Frenken; Cornelis Theodorus Verrips, both of Vlaardingen (NL)

(73) Assignee: Lever Brothers Company, Division of Conopco, Inc., New York, NY (US)

( * ) Notice: Subject to any disclaimer, the term of this patent is extended or adjusted under 35 U.S.C. 154(b) by 0 days.

(21) Appl. No.: 09/094,648

(22) Filed: Jun. 15, 1998

(30) Foreign Application Priority Data

Jun. 13, 1997 (EP) ........................................ 97304145

(51) Int. Cl.$^7$ ........................ C11D 3/00; A61K 38/43

(52) U.S. Cl. .................... 510/305; 510/300; 510/320; 510/321; 510/374; 510/392; 510/393; 510/530; 424/94.1; 252/186.1

(58) Field of Search ............................ 510/305, 300, 510/320, 321, 374, 392, 393, 530; 424/94.1; 252/186.1

(56) References Cited

U.S. PATENT DOCUMENTS

| | | | | |
|---|---|---|---|---|
| 4,919,811 | | 4/1990 | Davis . | |
| 5,904,735 | * | 5/1999 | Gutierrez et al. | 8/137 |
| 5,912,405 | * | 6/1999 | Scheider et al. | 8/111 |
| 6,080,573 | | 6/2000 | Convents et al. | 435/263 |

FOREIGN PATENT DOCUMENTS

| | | |
|---|---|---|
| 070 074 | 7/1982 | (EP) . |
| 258 068 | 8/1987 | (EP) . |
| 346 995 | 6/1989 | (EP) . |
| 450 702 | 3/1991 | (EP) . |
| 328 177 | 1/1999 | (EP) . |
| 2 101 167 | 5/1982 | (GB) . |
| 2107167 | 3/1997 | (GB) . |
| 89/09813 | 10/1989 | (WO) . |
| 0 540 784 A1 | 11/1991 | (WO) . |
| 94/25591 | 10/1994 | (WO) . |
| 94/25591 | 11/1994 | (WO) . |
| 94/29457 | 12/1994 | (WO) . |
| 95/01426 | 1/1995 | (WO) . |
| 95/07972 | 3/1995 | (WO) . |
| 95/29996 | 11/1995 | (WO) . |
| 97/04102 | 2/1997 | (WO) . |
| 97/11217 | 3/1997 | (WO) . |

* cited by examiner

*Primary Examiner*—Arlen Soderquist
*Assistant Examiner*—Monique T. Cole
(74) *Attorney, Agent, or Firm*—Rimma Mitelman

(57) ABSTRACT

There is provided a bleaching enzyme capable of generating a bleaching chemical and having a high binding affinity for stains present on fabrics. Furthermore, there is provided an enzymatic bleaching composition comprising the bleaching enzyme and a surfactant and a process for bleaching stains present of fabrics.

17 Claims, 7 Drawing Sheets

Figure 1:
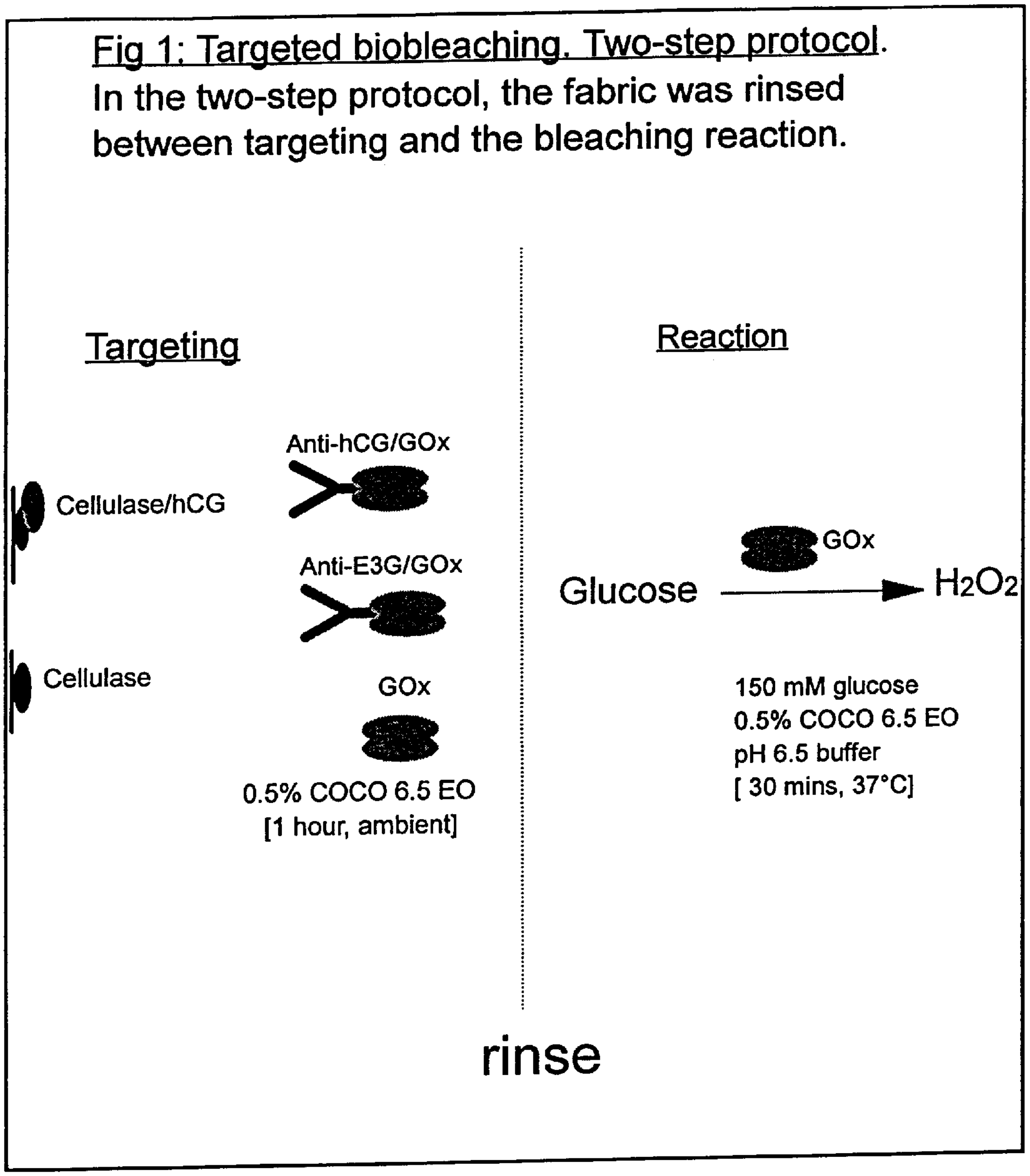

Fig 1: Targeted biobleaching. Two-step protocol.
In the two-step protocol, the fabric was rinsed between targeting and the bleaching reaction.

Figure 2:
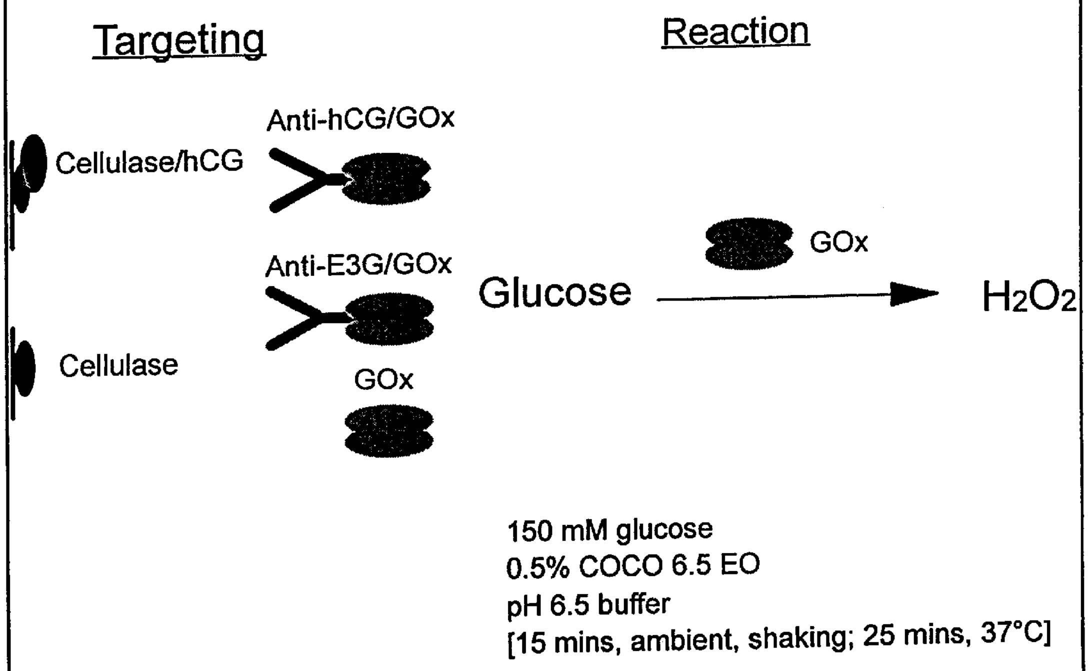

Fig 2: Targeted biobleaching. One-step protocol.

In the one-step protocol, there was not a rinsing step between targeting and the bleaching reaction. Therefore, targeting and bleaching took place in the same medium.

BLEACHING ENZYMES

TECHNICAL FIELD

The present invention generally relates to bleaching enzymes. More in particular, it relates to bleaching enzymes capable of generating a bleaching chemical and having a high binding affinity for stains present on fabrics. The invention also relates to a detergent composition comprising said enzymes and to a process for bleaching stains present on fabrics.

BACKGROUND AND PRIOR ART

Detergent compositions comprising bleaching enzymes have been described in the prior art. For instance, GB-A-2 101 167 (Unilever) discloses an enzymatic bleach composition in the form of a hydrogen peroxide-generating system comprising a $C_1$–$C_4$ alkanol oxidase and a $C_1$–$C_4$ alkanol. Such enzymatic bleach compositions may be used in detergent compositions for fabric washing, in which they may provide a low-temperature enzymatic bleach system. In the wash liquor, the alkanol oxidase enzyme catalyses the reaction between dissolved molecular oxygen and the alkanol to form an aldehyde and hydrogen peroxide. In order to obtain a significant bleach effect at low wash temperatures, e.g. at 15–55° C., the hydrogen peroxide must be activated by means of a bleach activator. Today, the most commonly used bleach activator is tetra-acetyl ethylene diamine (TAED), which yields peracetic acid upon reacting with the hydrogen peroxide, the peracetic acid being the actual bleaching agent.

Although this and several other enzymatic bleach systems have been proposed, there is still a need for alternative or improved enzymatic bleach systems. In particular, the enzymatic bleach system should be capable of bleaching stains which are otherwise difficult to remove, the so-called "problem stains" such as tea, blackberry juice, or red wine. Such stains would require a significant amount of bleaching for their removal, which might negatively affect the colours of the garment.

In conventional laundry bleach systems, fabrics are uniformly exposed to the same concentration of bleach, whether "problem stains" are present or not. Moreover, damage to garments (such as the fading of dyes) can be caused by repeated washing with conventional bleach systems, which may contain relatively high concentrations of bleach.

It is therefore an object of the present invention to provide alternative or improved enzymatic bleach systems which, in particular, should be capable of bleaching stains which are otherwise difficult to remove, and should preferably be more selective in its bleaching action. It is a further object of the present invention to provide an alternative or improved enzymatic bleach process.

We have now surprisingly found that it is possible to control the enzymatic bleaching reaction by using the bleaching enzyme according to the invention, which is capable of generating a bleaching chemical and has a high binding affinity for stains present on fabrics. Preferably, the enzyme comprises an enzyme part capable of generating a bleaching chemical, coupled to a reagent having a high binding affinity for stains present on fabrics.

The new bleaching enzyme is particularly attractive for treating "problem stains" which occur only occasionally, such as tea, red-wine, and blackberry juice. These stains are not present on most garments and when they are present they are likely to be present in different positions than habitual stains such as those found on collars and cuffs. According to the invention, it is possible to optimise the in-use concentration of the new bleaching enzyme so that threshold concentrations of bleach are only reached if stain is present and the new bleaching enzyme binds to and accumulates on said stain.. When this happens, the high local concentration of enzyme generates a high local concentration of bleach near to the stain and thereby exerts a selective bleaching action where it is required. Therefore, the unstained part of the garment (typically the majority) is not exposed to high levels of bleach and thereby this fabric is protected from bleach-associated damage. Moreover, the next time the same garment has a stain such as blackberry, tea, wine, etc. it is likely to be in a different position on the garment. Therefore, a different position on the garment will be exposed to high levels of bleach. Therefore, problems associated with several washes in conventional bleaching systems, such as dye-fade, will be reduced or eliminated altogether. This is in stark contrast to conventional bleaching systems where all garments are uniformly exposed to high concentrations of bleach, in every wash, regardless of whether problem stains are present or not.

DEFINITION OF THE INVENTION

According to a first aspect of the invention, there is provided a bleaching enzyme capable of generating a bleaching chemical and having a high binding affinity for stains present on fabrics. Preferably, the enzyme comprises an enzyme part capable of generating a bleaching chemical, coupled to a reagent having a high binding affinity for stains present on fabrics.

According to a second aspect, there is provided an enzymatic bleaching composition comprising one or more surfactants and the bleaching enzyme according to the invention.

According to a third aspect, there is provided a process for bleaching stains present of fabrics, wherein stained fabrics are contacted with an a solution comprising the bleaching enzyme of the invention.

DESCRIPTION OF THE INVENTION

1. The Bleaching Enzyme

In its first aspect, the invention relates to a bleaching enzyme which is capable of generating a bleaching chemical and has a high binding affinity for stains present on fabrics. Preferably, the enzyme comprises an enzyme part capable of generating a bleaching chemical which is coupled to a reagent having a high binding affinity for stains present on fabrics.

1.1 The Enzyme Part, Capable of Generating a Bleaching Chemical

The bleaching chemical may be enzymatically generated hydrogen peroxide. The enzyme for generating the bleaching chemical or enzymatic hydrogen peroxide-generating system may in principle be chosen from the various enzymatic hydrogen peroxide-generating systems which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. Alternatively, a combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative

*Hansenula polymorpha* strain. (see for example EP-A-244 920 (Unilever)). The preferred oxidases are glucose oxidase, galactose oxidase and alcohol oxidase.

A hydrogen peroxide generating enzyme could be used in combination with activators which generate peracetic acid. Such activators are well-known in the art. Examples include tetraacetylethylenediamine (TAED) and sodium nonanoyloxybenzenesulphonate (SNOBS). These and other related compounds are described in fuller detail by Grime and Clauss in Chemistry & Industry (Oct. 15, 1990) 647–653. Alternatively, a transition metal catalyst could be used in combination with a hydrogen peroxide generating enzyme to increase the bleaching power. Examples of manganese catalysts are described by Hage et al. (1994) Nature 369, 637–639.

Alternatively, the bleaching chemical is hypohalite and the enzyme part is then a haloperoxidase. Preferred haloperoxidases are chloroperoxidases and the corresponding bleaching chemical is hypochlorite. Especially preferred chloroperoxidases are Vanadium chloroperoxidases, for example from *Curvularia inaegualis.*

Alternatively, peroxidases or laccases may be used. In this case the bleaching molecule is derived from an enhancer molecule that has reacted with the enzyme. Examples of laccase/enhancer systems are given in WO-A-95/01426. Examples of peroxidase/enhancer systems are given in WO-A-97/11217.

1.2 The Part Having the High Binding Affinity

The new bleaching enzyme has a high binding affinity for stains present on fabrics. It may be that one part of the polypeptide chain of the bleaching enzyme is responsible for the binding affinity, but it is also possible that the enzyme comprises an enzyme part capable of generating a bleaching chemical which is coupled to a reagent having the high binding affinity for stains present on fabrics. In the first situation, the bleaching enzyme may be a fusion protein comprising two domains which may be coupled by means of a linker. In the second situation, the reagent having the high binding affinity may be covalently coupled to the enzyme part for generating the bleaching chemical, by means of a bi-valent coupling agent such as glutardialdehyde. A full review of chemistries appropriate for coupling two biomolecules is provided in "Bioconjugate techniques" by Greg T. Hermanson, Academic Press Inc (1986). Alternatively, if the reagent having the high binding affinity is a peptide or a protein, it may also be coupled to the enzyme by constructing a fusion protein. In such a construct there would typically be a peptide linker between the binding reagent and the enzyme. An example of a fusion of an enzyme and a binding reagent is described in Ducancel et al. Bio/technology 11, 601–605.

A further embodiment would be for the reagent with a high binding affinity to be a bispecific reagent, comprising one specificity for stain and one for enzyme. Such a reagent could fulfill the requirement of accumulating enzyme on stain either by supplying said reagent together with enzyme as a pre-formed non-covalent complex or by supplying the two separately and allowing them to self-assemble either in the wash liquor or on the stain.

The novel bleaching enzyme according to the invention is based on the presence of a part having a high binding affinity for stains present on fabrics.

The degree of binding of a compound A to another molecule B can be generally expressed by the chemical equilibrium constant $K_d$ resulting from the following reaction:

$$[A]+[B] \leftrightarrow [A \equiv B]$$

The chemical equilibrium constant $K_d$ is then given by:

$$K_d = \frac{[A] \times [B]}{[A \equiv B]}$$

Whether the binding to the stains is specific or not can be judged from the difference between the binding ($K_d$ value) of the compound to stained (i.e. a material treated so that stain components are bound on), versus the binding to unstained (i.e. untreated) material, or versus the binding to material stained with an unrelated chromophore. For applications in laundry, said material will be a fabric such as cotton or polyester. However, it will usually be more convenient to measure $K_d$ values and differences in $K_d$ values on other materials such as a polystyrene microtitre plate or a specialised surface in an analytical biosensor. The difference between the two binding constants should be minimally 10, preferably more than 100, and more preferably, more that 1000. Typically, the compound should bind the stain, or the stained material, with a Kd lower than $10^{-5}$ M, preferably lower than $10^{-6}$ M and could be $10^{-10}$ M or even less. Higher binding affinities (Kd of less than $10^{-5}$M) and/or a larger difference between coloured substance and background binding would increase the selectivity of the bleaching process. Also, the weight efficiency of the compound in the total detergent composition would be increased and smaller amounts of the compound would be required.

Several classes of compounds can be envisaged which deliver the capability of specific binding to stains one would like to bleach. In the following we will give a number of examples of such compounds having such capabilities, without pretending to be exhaustive.

1.2.1. Antibodies

Antibodies are well known examples of compounds which are capable of binding specifically to compounds against which they were raised. Antibodies can be derived from several sources. From mice, monoclonal antibodies can be obtained which possess very high binding affinities. From such antibodies, Fab, Fv or scFv fragments, can be prepared which have retained their binding properties. Such antibodies or fragments can be produced through recombinant DNA technology by microbial fermentation. Well known production hosts for antibodies and their fragments are yeast, moulds or bacteria.

A class of antibodies of particular interest is formed by the Heavy Chain antibodies as found in Camelidae, like the camel or the llama. The binding domains of these antibodies consist of a single polypeptide fragment, namely the variable region of the heavy chain polypeptide (HC-V). In contrast, in the classic antibodies (murine, human, etc.), the binding domain consist of two polypeptide chains (the variable regions of the heavy chain ($V_h$) and the light chain ($V_l$)). Procedures to obtain heavy chain immunoglobulins from Camelidae, or (functionalized) fragments thereof, have been described in WO-A-94/04678 (Casterman and Hamers) and WO-A-94/25591 (Unilever and Free University of Brussels).

Alternatively, binding domains can be obtained from the $V_h$ fragments of classical antibodies by a procedure termed "camelization". Hereby the classical $V_h$ fragment is transformed, by substitution of a number of amino acids, into a HC-V-like fragment, whereby its binding properties are retained. This procedure has been described by Riechmann et al. in a number of publications (J. Mol. Biol. (1996) 259, 957–969; Protein. Eng. (1996) 9, 531–537, Bio/Technology (1995) 13, 475–479). Also HC-V fragments can be produced through recombinant DNA technology in a number of microbial hosts (bacterial, yeast, mould), as described in WO-A-94/29457 (Unilever).

Methods for producing fusion proteins that comprise an enzyme and an antibody or that comprise an enzyme and an antibody fragment are already known in the art. One approach is described by Neuberger and Rabbits (EP-A-194 276). A method for producing a fusion protein comprising an enzyme and an antibody fragment that was derived from an antibody originating in Camelidae is described in WO-A-94/25591. A method for producing bispecific antibody fragments is described by Holliger et al. (1993) PNAS 90, 6444–6448.

A particularly attractive feature of antibody binding behavior is their reported ability to bind to a "family" of structurally-related molecules. For example, in Gani et al. (J. Steroid Biochem. Molec. Biol. 48, 277–282) an antibody is described that was raised against progesterone but also binds to the structurally-related steroids, pregnanedione, pregnanolone and 6-hydroxy-progesterone. Therefore, using the same approach, antibodies could be isolated that bind to a whole "family" of stain chromophores (such as the polyphenols, porphyrins, or caretenoids as described below). A broad action antibody such as this could be used to treat several different stains when coupled to a bleaching enzyme.

1.2.2. Peptides

Peptides usually have lower binding affinities to the substances of interest than antibodies. Nevertheless, the binding properties of carefully selected or designed peptides can be sufficient to deliver the desired selectivity in a oxidation process. A peptide which is capable of binding selectively to a substance which one would like to oxidise, can for instance be obtained from a protein which is known to bind to that specific substance. An example of such a peptide would be a binding region extracted from an antibody raised against that substance. Other examples are proline-rich peptides that are known to bind to the polyphenols in wine.

Alternatively, peptides which bind to such substance can be obtained by the use of peptide combinatorial libraries. Such a library may contain up to 1010 peptides, from which the peptide with the desired binding properties can be isolated. (R. A. Houghten, Trends in Genetics, Vol 9, no &, 235–239). Several embodiments have been described for this procedure (J. Scott et al., Science (1990) 249, 386–390; Fodor et al., Science (1991) 251, 767–773; K. Lam et al., Nature (1991) 354, 82–84; R. A. Houghten et al., Nature (1991) 354, 84–86).

Suitable peptides can be produced by organic synthesis, using for example the Merrifield procedure (Merrifield (1963) J. Am. Chem. Soc. 85, 2149–2154). Alternatively, the peptides can be produced by recombinant DNA technology in microbial hosts (yeast, moulds, bacteria) (K. N. Faber et al. (1996) Appl. Microbiol. Biotechnol. 45, 72–79).

1.2.3. Pepidomimics

In order to improve the stability and/or binding properties of a peptide, the molecule can be modified by the incorporation of non-natural amino acids and/or non-natural chemical linkages between the amino acids. Such molecules are called peptidomimics (H.U. Saragovi et al. (1991) Bio/Technology 10, 773–778; S. Chen et al. (1992) Proc. Natl. Acad. Sci. USA 89, 5872–5876). The production of such compounds is restricted to chemical synthesis.

1.2.4. Other Organic Molecules

It can be readily envisaged that other molecular structures, which need not be related to proteins, peptides or derivatives thereof, can be found which bind selectively to substances one would like to oxidise with the desired binding properties. For example, certain polymeric RNA molecules which have been shown to bind small synthetic dye molecules (A. Ellington et al. (1990) Nature 346, 818–822). Such binding compounds can be obtained by the combinatorial approach, as described for peptides (L. B. McGown et al. (1995), Analytical Chemistry, 663A-668A)

This approach can also be applied for purely organic compounds which are not polymeric. Combinatorial procedures for synthesis and selection for the desired binding properties have been described for such compounds (Weber et al. (1995) Angew. Chem. Int. Ed. Engl. 34, 2280–2282; G. Lowe (1995), Chemical Society Reviews 24, 309–317; L. A. Thompson et al. (1996) Chem. Rev. 96, 550–600). Once suitable binding compounds have been identified, they can be produced on a larger scale by means of organic synthesis.

1.3 The Stains

For detergents applications, several classes of coloured substances one would like to bleach can be envisaged, in particular coloured substances which may occur as stains on fabrics can be a target. However, it is also important to emphasise that many stains are heterogeneous. Therefore, the substance to be targeted need not itself be coloured providing that it is always present in the mixture of substances that constitute a stain.

Moreover, an important embodiment of the invention is to use a binding compound (refer to 1.2) that binds to several different, but structurally-related, molecules in a class of "stain substances". This would have the advantage of enabling a single enzyme species to bind (and bleach) several different stains. An example would be to use an antibody which binds to the polyphenols in wine, tea, and blackberry. Further examples of classes of stain substances are given below:

1.3.1. Porphyrin Derived Structures

Porphyrin structures, often co-ordinated to a metal, form one class of coloured substances which occur in stains. Examples are heme or haematin in blood stain, chlorophyll as the green substance in plants, e.g. grass or spinach. Another example of a metal-free substance is bilirubin, a yellow breakdown product of heme.

1.3.2. Tannins, Polyphenols

Tannins are polymerised forms of certain classes of polyphenols. Such polyphenols are catechins, leuantocyanins, etc. (P. Ribéreau-Gayon, Plant Phenolics, Ed. Oliver & Boyd, Edinburgh, 1972, pp.169–198). These substances can be conjugated with simple phenols like e.g. gallic acids. These polyphenolic substances occur in tea stains, wine stains, banana stains, peach stains, etc. and are notoriously difficult to remove.

1.3.3. Carotenoids (G. E. Bartley et al. (1995), The Plant Cell 7, 1027–1038). Carotenoids are the coloured substances which occur in tomato (lycopene, red), mango (β-carotene, orange-yellow). They occur in food stains (tomato) which are also notoriously difficult to remove, especially on coloured fabrics, when the use of chemical bleaching agents is not advised.

1.3.4. Anthocyanins (P. Ribereau-Gayon, Plant Phenolics, Ed. Oliver & Boyd, Edinburgh, 1972, 135–169). These substance are the highly coloured molecules which occur in many fruits and flowers. Typical examples, relevant for stains, are berries, but also wine. Anthocyanins have a high diversity in glycosidation patterns.

1.3.5. Maillard Reaction Products

Upon heating of mixtures of carbohydrate molecules in the presence of protein/peptide structures, a typical yellow/brown coloured substance arises. These substances occur for example in cooking oil and are difficult to remove from fabrics.

2. The Detergent Composition

The bleaching enzymes can be used in a detergent composition, specifically suited for stain bleaching purposes, and this constitutes a second aspect of the invention. To that extent, the composition comprises a surfactant and optionally other conventional detergent ingredients. The invention in its second aspect provides an enzymatic detergent composition which comprises from 0.1–50% by weight, based on the total detergent composition, of one or more surfactants. This surfactant system may in turn comprise 0–95% by weight of one or more anionic surfactants and 5–100% by weight of one or more nonionic surfactants. The surfactant system may additionally contain amphoteric or zwitterionic detergent compounds, but this in not normally desired owing to their relatively high cost. The enzymatic detergent composition according to the invention will generally be used as a dilution in water of about 0.05 to 2%.

In general, the nonionic and anionic surfactants of the surfactant system may be chosen from the surfactants described "Surface Active Agents" Vol. 1, by Schwartz & Perry, Interscience 1949, Vol. 2 by Schwartz, Perry & Berch, Interscience 1958, in the current edition of "McCutcheon's Emulsifiers and Detergents" published by Manufacturing Confectioners Company or in "Tenside- Taschenbuch", H. Stache, 2nd Edn., Carl Hauser Verlag, 1981.

Suitable nonionic detergent compounds which may be used include, in particular, the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are $C_6$–$C_{22}$ alkyl phenol-ethylene oxide condensates, generally 5 to 25 EO, i.e. 5 to 25 units of ethylene oxide per molecule, and the condensation products of aliphatic $C_8$–$C_{18}$ primary or secondary linear or branched alcohols with ethylene oxide, generally 5 to 40 EO.

Suitable anionic detergent compounds which may be used are usually water-soluble alkali metal salts of organic sulphates and sulphonates having alkyl radicals containing from about 8 to about 22 carbon atoms, the term alkyl being used to include the alkyl portion of higher acyl radicals. Examples of suitable synthetic anionic detergent compounds are sodium and potassium alkyl sulphates, especially those obtained by sulphating higher $C_8$–$C_{18}$ alcohols, produced for example from tallow or coconut oil, sodium and potassium alkyl $C_9$–$C_{20}$ benzene sulphonates, particularly sodium linear secondary alkyl $C_{10}$–$C_{15}$ benzene sulphonates; and sodium alkyl glyceryl ether sulphates, especially those ethers of the higher alcohols derived from tallow or coconut oil and synthetic alcohols derived from petroleum. The preferred anionic detergent compounds are sodium $C_{11}$–$C_{15}$ alkyl benzene sulphonates and sodium $C_{12}$–$C_{18}$ alkyl sulphates. Also applicable are surfactants such as those described in EP-A-328 177 (Unilever), which show resistance to salting-out, the alkyl polyglycoside surfactants described in EP-A-070 074, and alkyl monoglycosides.

Preferred surfactant systems are mixtures of anionic with nonionic detergent active materials, in particular the groups and examples of anionic and nonionic surfactants pointed out in EP-A-346 995 (Unilever). Especially preferred is surfactant system which is a mixture of an alkali metal salt of a $C_{16}$–$C_{18}$ primary alcohol sulphate together with a $C_{12}$–$C_{15}$ primary alcohol 3–7 EO ethoxylate.

The nonionic detergent is preferably present in amounts greater than 10%, e.g. 25–90% by weight of the surfactant system. Anionic surfactants can be present for example in amounts in the range from about 5% to about 40% by weight of the surfactant system.

The detergent composition may take any suitable physical form, such as a powder, an aqueous or non aqueous liquid, a paste or a gel.

The bleaching enzyme used in the present invention can usefully be added to the detergent composition in any suitable form, i.e. the form of a granular composition, a liquid or a slurry of the enzyme, or with carrier material (e.g. as in EP-A-258 068 and the Savinase (TM) and Lipolase (TM) products of Novo Nordisk). A good way of adding the enzyme to a liquid detergent product is in the form of a slurry containing 0.5 to 50% by weight of the enzyme in a ethoxylated alcohol nonionic surfactant, such as described in EP-A-450 702 (Unilever).

The enzymatic bleaching compositions of the invention comprise about 0.001 to 10 milligrams of active bleaching enzyme per liter. A detergent composition will comprise about 0.001% to 1% of active enzyme (w/w).

The enzyme activity can be expressed in units. For example, in the case of glucose oxidase, one unit will oxidise 1 $\mu$ mole of β-D-glucose to D-gluconolactone and $H_2O_2$ per minute at pH 6.5 at 30° C. The enzyme activity which is added to the enzymatic bleaching composition will be about 2.0 to 4,000 units per litre (of wash liquor).

The invention will now be further illustrated in the following, non-limiting Examples.

In the Figures is:

FIG. 1: Two-step protocol. In the two-step protocol, the fabric was rinsed between targetting and the bleaching reaction.

FIG. 2: One-step protocol. In the one-step protocol, there was not a rinsing step between targetting and the bleaching reaction. Therefore, targetting and bleaching took place in the same medium.

Figure 3:
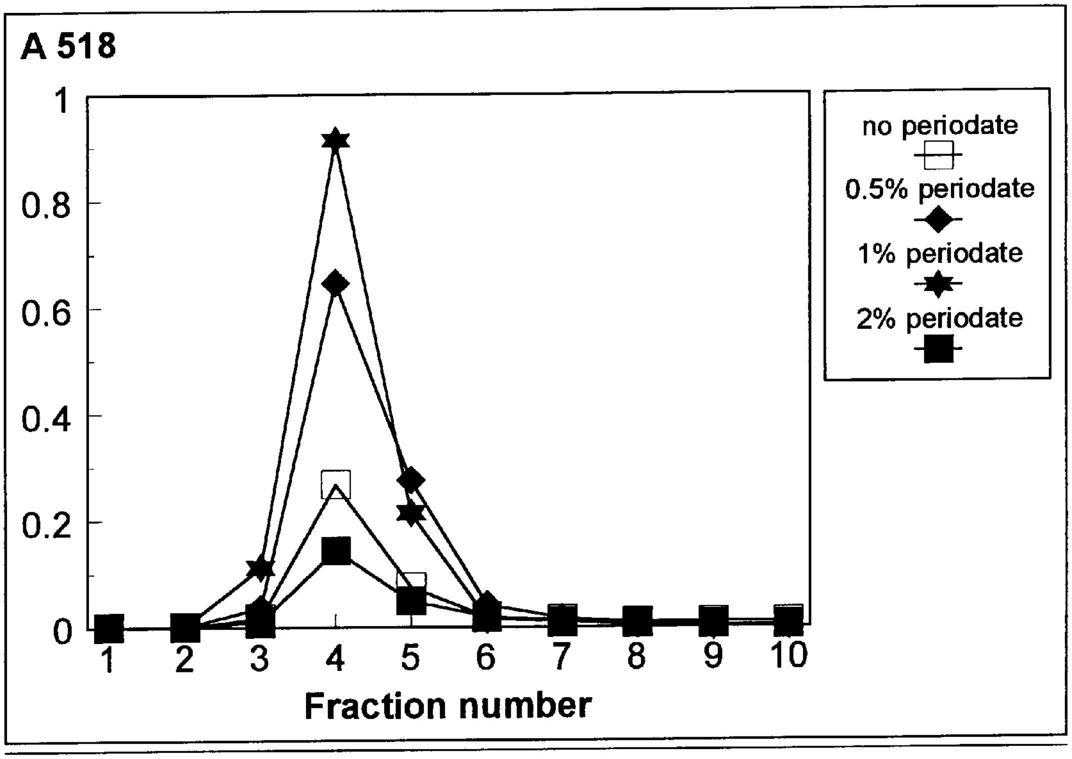

FIG. 3: Analysis of BSA-wine immunogen by chromatography on G25 Sephadex.

Figure 4:
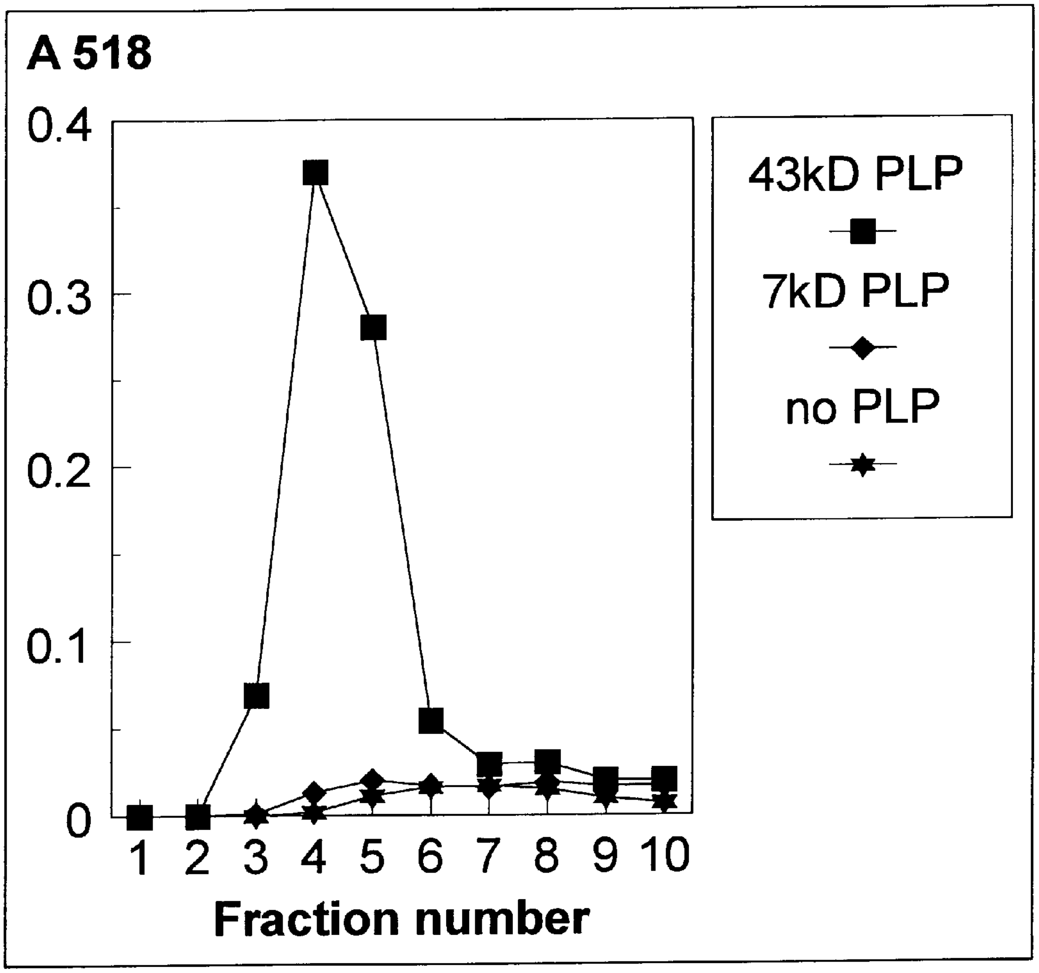

FIG. 4: Analysis of PLP/wine mixtures by chromatogaphy on G25 Sephadex.

Figure 5:
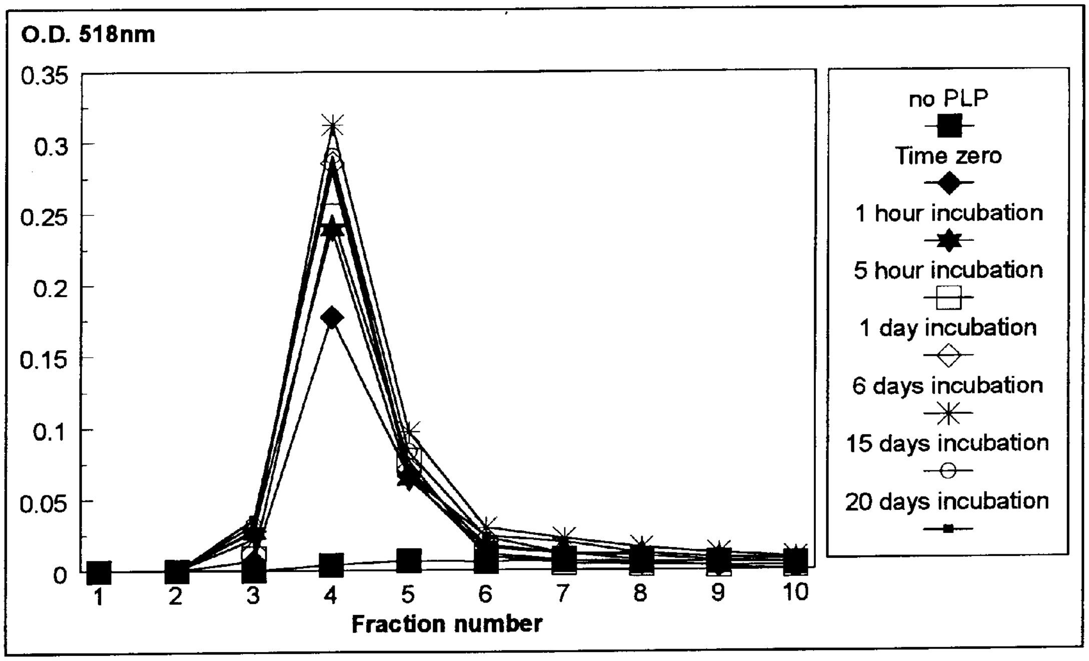

FIG. 5: Investigation of stability of non-covalent complex formed between poly-L-proline and wine pigments.

Figure 6:
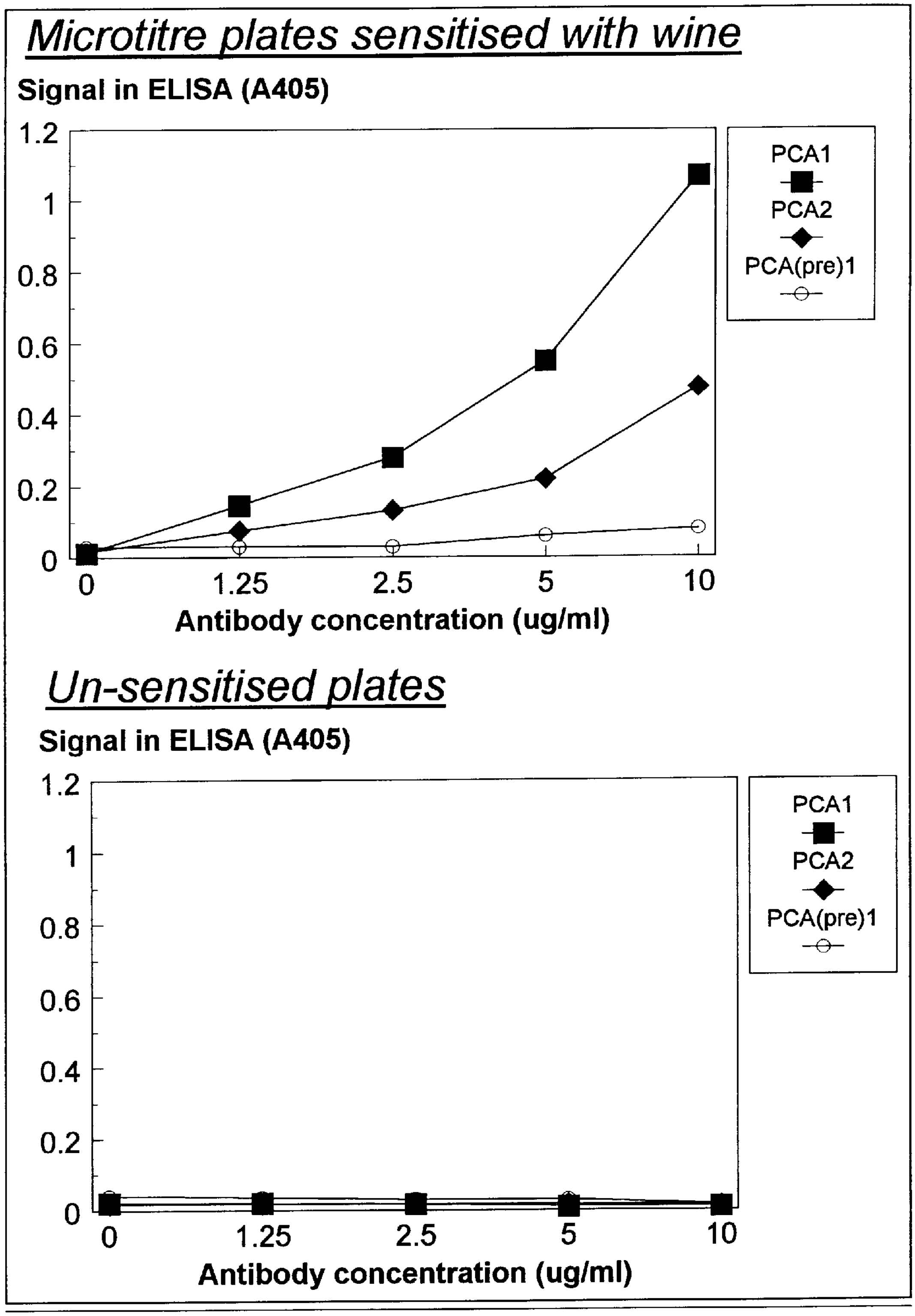

FIG. 6: Analysis of antibody binding to red wine.

Figure 7:
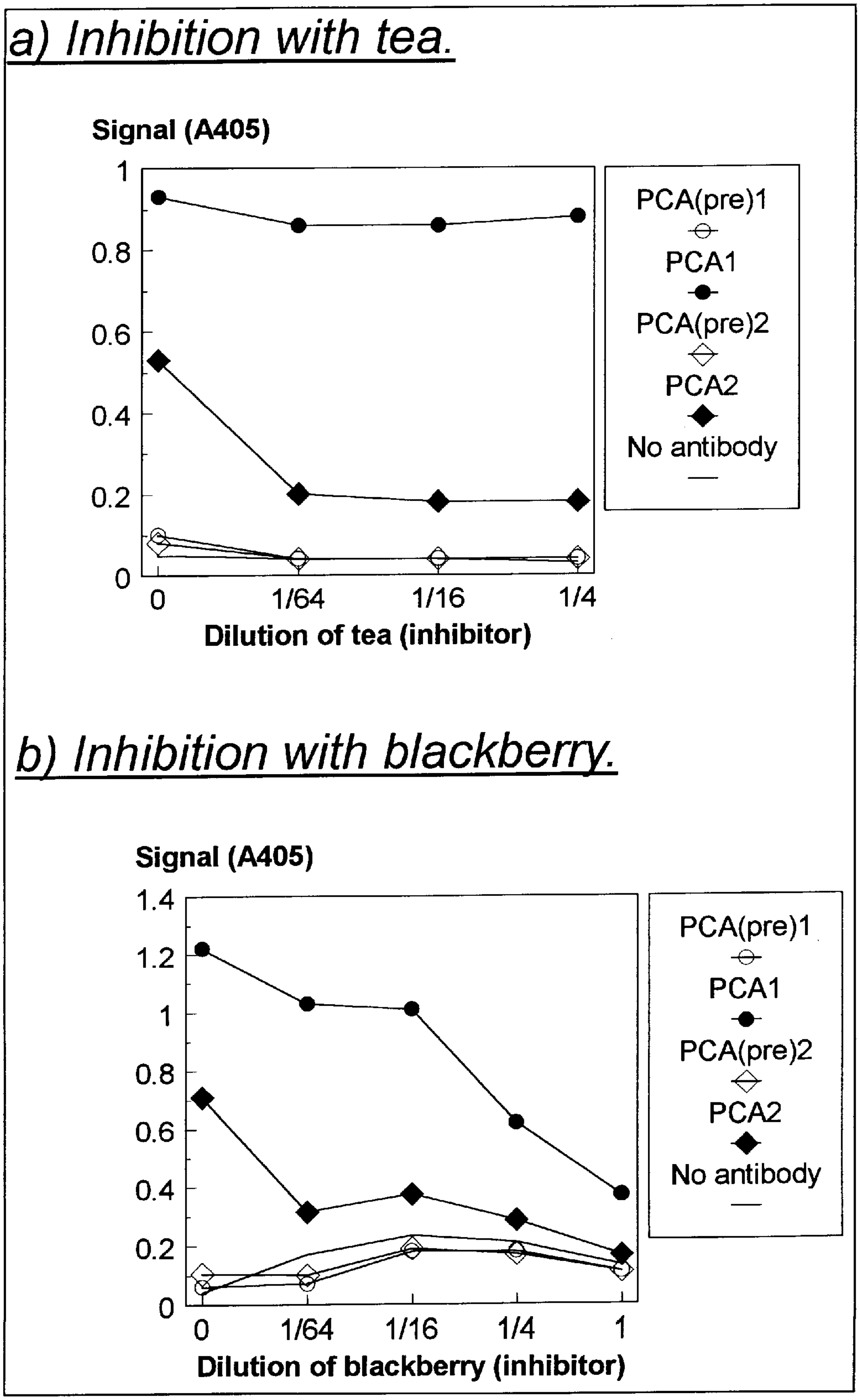

FIG. 7: Cross-reactivity of wine-binding antibodies with other polyphenol-containing foodstuffs that are known to produce problem stains. Cross-reactivity was determined by inhibition analysis.

EXAMPLE 1

Use of a Scaled-down Model to Illustrate the Benefits of Targeted Bio-bleaching The following examples 1–5 comprise a scaled-down model system in which a red wine stain on cotton fabric was labelled with a protein antigen for which an antibody is already available. The antibody was covalently coupled to glucose oxidase enzyme using standard procedures, to form an antibody/oxidase conjugate. This conjugate was then applied to the (labelled) wine stain in the presence of glucose. The glucose oxidase enzyme generated $H_2O_2$ close to the surface of the stain and bleached it. The amount of bleaching was compared with that obtained with the same amount of unconjugated (and therefore untargeted) glucose oxidase. It was also compared with the bleaching obtained by the same amount of glucose oxidase conjugated to a non-specific antibody that did not bind to the protein label. It was also found that particularly good targeting effects could be achieved if the conjugate and glucose were applied in two steps with a rinse in between.

It will be apparent to anyone skilled in the art that methods are available to raise antibodies to small organic molecules. See for example Gani et al. (J. Steroid Biochem. Molec. Biol. 48, 277–282), where antibodies are raised to steroids. Therefore, antibodies could be raised to the constituents of stains by the using the same technical approach. Molecules of interest would include the polyphenols in wine, tea, and blackberry; or the porphyrin rings in blood and grass. Moreover, some antibodies raised against small organic molecules cross-react with other similar structures. For example, in Gani et al. an antibody is described which was raised against progesterone and also binds to the structurally-related steroids, pregnanedione, pregnanolone and 6-hydroxy-progesterone. Therefore, using the same approach, antibodies could be isolated that bind to the polyphenols in red wine and also to the polyphenols in tea and blackberry. Once such antibodies have been made, their coupling to glucose oxidase and applying to stain would be as below. However, when using these antibodies it would not be necessary to label the stain with protein antigen.

EXAMPLE 2

Labelling Stains with Protein Antigen

White cotton fabric was stained with red wine (Cótes du Rhône, Co-op) and dried in a 37° C. incubator. Stained fabric was cut into 1 cm squares and then labelled with a protein antigen, human chorionic gonadotropin (hCG). This was done by applying hCG in the form of a cellulase/hCG conjugate (cellulase binds to cotton fabric). The conjugate was prepared by methods that are well known in the art (see for example "Bioconjugate Techniques" by Greg T. Hermanson, Academic Press (1996)).

Cellulase ex. *Trichoderma reesei*, (Sigma Product number C 8546) was derivatised with N-succinimidyl 3-(2-pyridyldithio) propionate, propionate, "SPDP", (Sigma). hCG (Sigma Product number C 5297) was derivatised with S-acetylmercaptosuccinic anhydride, "SAMSA" (Sigma). The two derivatised proteins were then reacted together in pH 6.5 buffer to yield a covalently-coupled conjugate.

The stained fabric squares were labelled with hCG by incubating them in a solution of the cellulase/hCG conjugate. The solution was approximately 10 μg/ml with respect to cellulase and was made up in phosphate buffered saline, PBS, [0.01M $Na_2HPO_4/NaH_2PO_4$-0.15M NaCl, pH 7]. The incubation was for 2 hours at 37° C. Control squares were also prepared that were incubated with cellulase only.

EXAMPLE 3

Preparation of Antibody/Glucose Oxidase Conjugates

Antibody/glucose oxidase conjugates were also prepared by the SAMSA/SPDP method. Antibody was derivatised with SAMSA and glucose oxidase was derivatised with SPDP. The two derivatised proteins were then reacted together in pH 6.5 buffer to yield a covalently-coupled conjugate. Two different antibodies were used: one that had a specificity for hCG, "anti-hCG antibody", and one that did not have a specificity for hCG, "anti-E3G antibody".

EXAMPLE 4

Targeted Bleaching of Red Wine Stain—Two-step Protocol

In the two-step protocol (see FIG. 1 for a schematic diagram), the fabric squares were rinsed between targeting and the bleaching reaction. The bleaching efficiency of the anti-hCG/glucose oxidase (Gox) conjugate was compared with that of anti-E3G glucose oxidase conjugate and glucose oxidase only.

Stained fabric squares, sensitised with either cellulase/hCG conjugate or cellulase only, were rinsed once with rinse buffer (PBS with 0.5% COCO 6.5 EO added as a surfactant) and then placed in a 24-well tissue culture plate (Costar). The squares were then treated with anti-hCG / glucose oxidase conjugate (in rinse buffer), anti-E3G / glucose oxidase conjugate (in rinse buffer), glucose oxidase (in rinse buffer), or rinse buffer only. The two conjugates had been normalised for glucose oxidase activity and were applied at a concentration equivalent to approximately 15 μg/ml of unconjugated enzyme. The fabric squares were left in these solutions for 1 hour at room temperature before rinsing them 3× with rinse buffer. The squares were then treated with substrate solution (150 mM glucose, 30 mM NaCl, 0.5% COCO 6.5 EO, 0.1M phosphate (pH 6.5)). The substrate solution was allowed to incubate with the fabric squares for 30 minutes at 37° C. Squares were removed from the substrate solution and dried overnight in a 37° C. incubator. Then the amount of stain removed was determined by using a "Color-eye 2020+" spectrophotometer (Macbeth). Fabric squares were read in triplicate and stain removal was recorded as ΔE (mean of the three readings) relative to stained, untreated fabric.

It was found that all the fabric squares that had been treated with untargeted glucose oxidase gave similar values for ΔE, see Table 1. These different untargeted formats were needed to make sure there were not any artefacts due to non-specific binding between any of the components in the 15 system. Given that all these untargeted formats gave similar readings, it was rigorous to take a mean of these readings, and record this as the mean untargeted enzyme score (ΔE=20.3, see table 1). The fabric squares that had been treated with targeted glucose oxidase gave a value of ΔE=25.3. The mean reading for squares treated with surfactant only was 18.9. (Table 1). Therefore, the untargeted glucose oxidase contributed an improvement of 1.4 units of de-stain above that already achieved by the surfactant in the system. In contrast, the targeted glucose oxidase contributed an improvement of 5.0 units. This means that targeting the glucose oxidase makes it 3.5-fold more effective at removing residual stains, i.e stains that can not be removed by surfactant alone.

EXAMPLE 5

Targeted Bleaching of Red Wine Stain—One-step protocol

In the one-step protocol (see FIG. 2 for a schematic diagram), there was no rinsing step between targeting and the bleaching reaction. Therefore, targeting and bleaching took place in the same medium. The bleaching efficiency of the anti-hCG/glucose oxidase conjugate was compared with that of anti-E3G/glucose oxidase and glucose oxidase only.

Samples of fabric (in triplicate) that had been sensitised with either cellulase/hCG conjugate or cellulase only were added to tubes containing 5 ml of antibody/glucose oxidase conjugate or glucose oxidase only. These were made up in "rinse+substrate buffer" (150 mM glucose, 30 mM NaCl, 0.5% COCO 6.5 EO, O.lM Phosphate (pH 6.5)). The tubes were shaken for 15 minutes at room temperature (to mix thoroughly and to allow the conjugates to bind) and then incubated for 25 minutes at 37° C. to allow bleaching to occur.

It is important to note that in the one-step protocol, the concentration of the conjugates was 100-fold lower than in the two-step protocol (approximately 0.15 μg/ml in terms of glucose oxidase). This reduction in concentration was needed to minimise non-specific binding effects that otherwise occur in the one-step protocol.

Reflectances were read in triplicate, as described earlier. The results are shown in Table 2. The targeted enzyme was found to produce stronger bleaching than untargeted enzyme, however, the improvement in bleaching that was attributable to targeting was less pronounced than that obtained with the two-step protocol.

TABLE 1

Bleaching to wine stained fabric with two-step protocol

| Sensitisation of stained cloth | Bleaching active(s) (applied in presence of surfactant) | Stain removal (ΔE) |
|---|---|---|
| Cellulase/ hCG conjugate | Anti-hCG/GOx conjugate [targeted system] | 25.3 |
| Cellulase | Anti-hCG/GOx conjugate [untargeted system] | 21.2 |
| Cellulase/ hCG conjugate | Anti-E3G/GOx conjugate [untargeted system] | 21.4 |
| Cellulase | Anti-E3G/GOx conjugate [untargeted system] | 20.0 |
| Cellulase/ hCG conjugate | Gox [untargeted system] | 19.9 |
| Cellulase | Gox [untargeted system] | 19.1 |
| Cellulase/ hCG conjugate | Surfactant only | 19.5 |
| Cellulase | Surfactant only | 18.3 |

[ΔE of white cloth = 30.6]
Mean targeted enzyme score = 25.3
Mean untargeted enzyme score = 20.3
Mean surfactant score = 18.9

TABLE 2

Bleaching of wine stained fabric with one-step protocol

| Sensitisation of stained cloth | Bleaching active(s) (applied in presence of surfactant) | Stain removal (ΔE) |
|---|---|---|
| Cellulase/ hCG conjugate | Anti-hCG/GOx conjugate [targeted system] | 22.0 |
| Cellulase | Anti-hCG/GOx conjugate [untargeted system] | 20.3 |
| Cellulase/ hCG conjugate | Anti-E3G/GOx conjugate [untargeted system] | 19.6 |
| Cellulase | Anti-E3G/GOx conjugate [untargeted system] | 20.3 |
| Cellulase/ hCG conjugate | GOx [untargeted system] | 19.2 |
| Cellulase | GOx [untargeted system) | 19.6 |
| Cellulase/ hCG conjugate | Surfactant only | 17.6 |
| Cellulase | Surfactant only | 17.3 |

[ΔE of white cloth = 30.6]
Mean targeted enzyme score = 22.0
Mean untargeted enzyme score = 19.8
Mean surfactant score = 17.5

EXAMPLE 6

In the following examples 6–17, red wine is used as the stain to be treated purely to illustrate how the invention may be carried out in practice. The invention is not limited to red wine stains and an analogous approach could be used to raise antibodies to other stains or to chemical constituents of stains.

The constituent chemicals in red wine have molecular masses of a few hundred Daltons (Saucier et al. (1997), Am. J. Enol. Vitic. 48, 370–373) and they are too small to raise an immune response themselves. Therefore, they need to be linked to a larger molecule, such as a protein, to make an "immunogen" i.e. a substance that is capable of generating an immune response. Linking small molecules to proteins to raise an immune response is a well-known technique. For example, Gani et al. (1994) J. Steroid Biochem. Molec. Biol. 48, 277–282 have linked steroids to Bovine Serum Albumin (BSA). In Examples 7–11, two immunogens comprising red wine were prepared and analysed: one was a covalent conjugate of red wine and BSA, the other was a non-covalent complex of red wine and poly-L-proline (PLP).

In Example 15, the wine-binding antibody is coupled to glucose oxidase by using chemical reagents that are marketed for purpose of cross-linking active proteins. However, it would also be possible to achieve the same effect by constructing a fusion protein from a stain-binding antibody and a bleaching enzyme, as described in the text.

EXAMPLE 7

Preparation of BSA-wine Covalent Conjugate

Red wine (Côtes du Rhône wine (Co-op, U.K.)) was adjusted to neutral pH with dilute NaOH and then 3ml was dispensed into each of 4 tubes. NaIO4 (Sigma) was freshly made up to 10% in water and then added drop-wise, in a fume-hood, to the four tubes so that they each contained different concentrations of periodate: 0%, 0.5%, 1% and 2%. The tubes were incubated overnight at room temperature and then each was mixed with an equal volume of BSA solution (2 mg/ml in MES buffer, pH 6.6). $NaBH_3$ CN (Aldrich) was made up to 10% and then added drop-wise, in a fume-hood, to each of the four tubes until the final concentration was equivalent to that of the periodate (i.e. 0%, 0.5%, 1%, or 2% as appropriate). The mixtures were incubated overnight at room temperature.

EXAMPLE 8

Analysis of BSA-wine Conjugate

A ml sample of each of the four preparations was analysed by gel permeation chromatography, using a PD10 disposable chromatography cartridge (Pharmacia). This cartridge comprises G25 Sephadex. A fresh cartridge was used for each sample. Each cartridge was conditioned in and eluted with phosphate buffered saline or "PBS" [0.01M $Na_2HPO_4$/ $NaH_2PO_4$-0.15M NaCl, pH 7]. Eluate was analysed by frontal analysis. 1 ml fractions were taken and analysed at 518 nm (the absorbance maximum for red pigments in wine). In the absence of periodate, there was some red pigment in the high molecular-weight fraction. This was presumably due to the formation of a non-covalent complex between BSA and wine anthocyanins. When periodate was present at 0.5% or 1%, several-fold more pigment was found in the high molecular-weight fraction. This was due to covalent attachment to albumin. When periodate was present at 2%, very little red pigment was seen in the high molecular-weight fraction. This was because this sample had developed a heavy precipitate—presumably due to extensive covalent cross-linking of wine pigments and BSA—and therefore could not pass down the column. (Refer to FIG. 3).

The conjugate prepared with 0.5% periodate was dialysed into 0.15M saline, filtered through an 0.2 μm filter (Sartorius) and then kept in the fridge until required for inoculating a rabbit. This was used in preference to the conjugate prepared with 1% periodate because the latter did not filter very easily, due to the presence of some precipitate.

EXAMPLE 9

Manipulation of the Interaction Between Wine Polyphenols and PLP.

Proline-rich peptides have been reported in the literature to precipitate polyphenols by multi-site interactions [Siebert et al. (1996) J. Agric. Food Chem. 44, 80–85; Sun and Mattro (1996) Polymer Bulletin 37, 691–698]. In the present study, it was sought to manipulate this reaction to form soluble complexes that would be suitable for inoculation. Two poly-l-proline (PLP) products were obtained from Sigma: a 7 kD product and a 43 kD product. The ratio of wine to PLP that was needed to avoid forming a precipitate was determined by mixing different amounts of wine (pH-neutralised and diluted in water) with different amounts of PLP (made up in PBS), incubating for 1 hour at 37° C., and then examining for formation of precipitate. It was found that under all conditions tested, the 7 kD product formed a precipitate; however, under some conditions, the 43 kD protein did not form a precipitate. See Table 3 below.

TABLE 3

Investigation of precipitate formation when mixing red wine with poly-L-proline (PLP).

| Vial | PLP type | PLP concentration | Wine concentration | Visible precipitate? (y/n) |
|---|---|---|---|---|
| 1 | 43 kD | 2 mg/ml | 50% | n |
| 2 | 7 kD | 2 mg/ml | 50% | y |
| 3 | 43 kD | 2 mg/ml | 100% | y |
| 4 | 7 kD | 2 mg/ml | 100% | y |
| 5 | 43 kD | 4 mg/ml | 50% | n |
| 6 | 7 kD | 4 mg/ml | 50% | y |

EXAMPLE 10

Analysis of PLP/wine Mixture for Soluble Complexes by Column Chromatograpghy

A mixture that did form a precipitate, was then investigated to see if it had instead formed a soluble complex (of PLP and wine polyphenols). Wine was pH-neutralised, diluted 1 in 2 in water, and then mixed with an equal volume of 2 mg/ml 43 kD PLP made up freshly in PBS. The mixture was incubated at 37° C. for 1 hour. The presence of complex was determined by gel permeation chromatography followed by frontal analysis at 518 nm, as described in Example 8. The chromatogram was compared with that obtained with red wine on its own or red wine mixed with 7 kD PLP under the same conditions. In the absence of PLP, the wine pigments bound to the column and did not elute off. However, the sample mixed with 43 kD PLP showed pigment to be present in the high molecular-weight fraction. Therefore, wine pigments and PLP must have been present in the form of a soluble complex. In contrast, the sample containing 7 kD PLP showed no pigment in the high molecular weight fraction. This was because this sample had formed a heavy precipitate and therefore could not migrate through the column (refer to FIG. 4).

The storage-stability of the complex made with 43 kD PLP was then investigated by storing a series of vials (containing said complex) at 37° C. and analysing by chromatography at intervals. The storage stability experiment showed that the interaction between wine pigments and PLP was complete in 1 hour and that no detectable dissociation of the complex had occurred even after 20 days at 37° C. (Refer to FIG. 5). Therefore, the complex was known to be stable at the temperature and for the approximate time-span that would be required for it to function as an immunogen (i.e. in vivo in the rabbit).

EXAMPLE 11

Preparation of PLP/wine Complex for Inoculation

An immunogen was prepared for inoculating a rabbit using conditions that were known not to form a precipitate. 43 kD PLP was made up to 2 mg/ml in PBS. Red wine was adjusted to approximately neutral pH with dilute NaOH and then diluted 1 in 4 in PBS. Then equal volumes of the wine and PLP were mixed together and then incubated for 1 hour at 37° C. The mixture was analysed on a PD10 column (as described in Example 10) to confirm it did indeed contain some soluble complex. It was then filtered through an 0.2 μm filter and then stored in the fridge until required for inoculation. Fresh immunogen was prepared for each booster inoculation.

EXAMPLE 12

Inoculation of Rabbits and Recovery of Antibody from Serum

One rabbit was inoculated with the BSA-wine conjugate and one with the polyproline/wine complex, hereafter referred to as rabbit 1 and rabbit 2 respectively. The dose given was lml at approximately lmg/ml protein. The first inoculation was given in Freund's complete adjuvant; further inoculations (or "boosters") were given approximately once per month in Freund's incomplete adjuvant.

A pre-bleed was taken from each rabbit prior to inoculation; test bleeds were taken for analysis about 10 days after each inoculation. Antibody was recovered from sera using a "Hi-Trap" Protein A cartridge (Pharmacia), according to manufacturer's instructions. These antibody preparations or "polyclonal antibodies" are hereafter referred to as PCA1 or PCA2 according to the rabbit from which they originated. Antibody preparations originating from the pre-bleeds are referred to PCA(pre)1 and PCA(pre)2. Antibody preparations were analysed for their ability to bind to constituents of red wine and to other polyphenols as described in Examples 13 and 14. When the analyses (refer to Examples 13 and 14) showed that there was a good immune response, a larger serum sample was prepared from the rabbit and used to make a big batch of antibody, again using a Hi-Trap Protein A cartridge. This antibody preparation was covalently linked to glucose oxidase enzyme as described in Example 15.

EXAMPLE 13

Analysis of Antibody Binding to Constituent Molecules of Red Wine

An Enzyme-linked Immunosorbent assay (ELISA) was assembled as follows: Untreated red wine was passed through an 0.2 μm filter (Sartorius) and then dispensed into the wells of microtitre plates (flat-bottomed, high capacity plates from Greiner labortechnik). The plates were then incubated at 37° C. overnight to promote adsorption of red wine molecules onto the surface of the wells. Plates that had been thus sensitised with wine were washed 3× with PBST [PBS+0.15% tween 20 (Sigma)] and then blocked with 1% chicken egg albumin (Sigma)—made up in PBST and filtered through an 0.2 μm filter (Sartorius). The blocking step was for 1 hour at room temperature. Control plates that had not been sensitised with wine were also treated with chicken egg albumin in the same way. Both sensitised and un-sensitised plates were then washed 3× in PBST before incubating with antibody (PCA1, PCA2, or PCA(pre)1, as defined in example 12). Dilutions of antibody ranged from 10 μg/ml to zero and were made up in PBST. Incubation with antibody was for 1 hour at room temperature.

Plates were washed 3× with PBST and then incubated with goat anti-rabbit/alkaline phosphatase conjugate (Zymed) made up in PBST. The incubation was for 1 hour at room temperature. Plates were washed 3× with PSBT and then incubated with substrate (1 mg/ml pNPP in 1M Diethylamine pH 9.8+1 mM $MgCl_2$). The incubation in substrate was continued until there was sufficient colour development (typically about 20 minutes). Absorbances was read at 450 nm in an automated ELISA reader. Both rabbits developed a good immune response to red wine: the antibodies recovered from both rabbits showed several properties that were characteristic of an efficient binding to wine. First, PCA1 and PCA2 bound to wine-sensitised microtitre plates in a concentration-dependent manner; secondly, PCA1 and PCA2 bound much more readily to wine-sensitised microtitre plates than did antibody recovered from a rabbit that had not (yet) been inoculated [i.e. PCA(pre)1]; thirdly, PCA1 and PCA2 bound more readily to wine-sensitised mirotitre plates than they did to un-sensitised plates. Moreover, when antibody was applied at 10 μg/ml, it could be seen that in the order of 100-fold more antibody had bound to sensitised plates than to un-sensitised plates. This shows that the antibodies had a much higher affinity for a surface impregnated with red wine than the same surface that had not been treated with wine. Refer to FIG. 6.

EXAMPLE 14

Analysis of Antibody Cross-reactivity to Other Stains

The ability of the antibody preparations to bind to other stucturally-related molecules, the polyphenols that are known to be present in wine and tea, was investigated by inhibition analysis. In this technique, antibody was pre-incubated with potential inhibitors (either wine or blackberry) and then applied to microtitre plates sensitised with wine. If binding to the wine was inhibited, the antibody was known to bind to the inhibitor as well. The experimental details are given below:

Solutions of antibodies PCA1, PCA2, PCA(pre)1 and PCA(pre)2 (as defined in Example 12) were made up to 10 μg/ml in twice-strength PBST (i.e. PBS+0.3% tween). Inhibitors [Tea (typhoo 2 g/liter) and blackberry juice (Budgen Ltd U.K.)] were clarified by centrifugation and filtration through a paper filter (Whatman No1). They were then filtered though an 0.2 μm filter (Sartorius) and diluted in water to make a range of concentrations from neat to 1/64. Each dilution of the inhibitors was mixed with each of the antibody solutions and then incubated at room temperature for 30 minutes. After this incubation, the "pre-incubation", the antibody was applied to a wine-sensitised microtitre plate and evaluated for binding as described in Example 13.

Binding of PCA2 to the wine-sensitised plate was inhibited by pre-incubation with tea; therefore, it was concluded that PCA2 binds to tea. Similarly, it was concluded that PCA1 does not bind to tea and that both PCA1 and PCA2 bind to blackberry. See FIG. 7. Therefore, both antibody preparations (PCA1 and PCA2) are broad-action reagents i.e. they can bind to more than one structurally-related compound, or to complex mixtures (such as foodstuffs) containing such compounds. Such reagents, when coupled to bleach-generating enzymes, can be used to treat more than one stain-type when present on fabric.

The finding that pre-incubation of PCA(pre)1 and PCA (pre)2 with tea or blackberry still did not result in said antibodies binding to the wine-sensitised plates was a useful negative control: it showed that no non-specific binding effects were introduced by the pre-incubation step.

EXAMPLE 15

Chemical Coupling of Antibody to Glucose Oxidase Enzyme

Stain-binding antibodies were chemically coupled to glucose oxidase using a method based on those described by Carlsson et al. (1978) Biochem. J. 173, 723–737 and by Hermanson in Bioconjugate Techniques, page 70–71. Antibody preparations PCA1 and PCA2 were concentrated to 10 mg/ml using Centricon 30 tubes (Amicon) and dialysed into 0.1M Phosphate buffer pH 6.5.

0.5 ml of each antibody (a total of 5 mg) was dispensed into a separate "reactivial" (a glass vial with a magnetic stirrer). 1.48 mg of "SAMSA" [s-acetylmercaptosuccinic anhydride, Sigma A1251] was added to each reactivial [SAMSA was added from a 25 mg/ml stock made up in dimethylformamide (Aldrich)] and the solutions were stirred at ambient temperature for 30 minutes. The following solutions were added to each reactivial at 5 minute intervals: 120 μl of 0.1M EDTA (after a total time of 35 minutes since adding the SAMSA); 480 μl of 0.1M Tris pH 7.0 (after 40 minutes); 480 μl of 1M hydroxylamine pH 7.0 (after 45 minutes). The volumes of each mixture were then made up to 2.5 ml with 0.1M phosphate buffer (after 50 minutes). Each of the two preparations were "desalted" by passing down a PD10 column (Pharmacia) that had been equilibrated in 0.1M phosphate+5 mM EDTA pH 6.5. A fresh column was used for each preparation. The purpose of the desalting step was to remove unreacted SAMSA and hydroxlyamine. A 3 ml protein fraction was collected from each column. Therefore, each fraction contained antibody (derivatised with SAMSA) at approximately 1.6 mg/ml.

A stock solution of Glucose oxidase (GOx) [Novo Nordisk. Glucose Oxidase ex. Aspergillus Niger, Product No. COO-05-85-1-del-1-PROs] was concentrated to 5 mg/ml and buffer exchanged into 0.1M phosphate pH 7.5 by passing down a PD10 column. 2 ml of this preparation (a total of 10 mg) was dispensed into a reactivial. 5 mg of "SPDP" [3-(2-Pyridyldithio)-propionic acid (Sigma P3415)] was dissolved in DMSO (dimethylsulfoxide, Sigma) and added to the GOx solution. The mixture was stirred at ambient temperature for 30 minutes. The preparation was then "desalted" by passing the solution down a PD 10 column equilibrated in 0.1M phosphate buffer pH 6.5. The purpose of the desalting step was to remove unreacted SPDP and to get the solution to the optimal pH for the conjugation reaction. A 3 ml protein fraction was collected from the column. Therefore, this fraction contained GOx (derivatised with SPDP) at approximately 3.3 mg/ml.

3 ml of each of the derivatised antibodies (at 1.6 mg/ml) were dispensed into separate glass vials. 1.5 ml of derivatised GOx (at 3.3 mg/ml) was added to each of the antibodies. The two mixtures were then placed at 4° C. overnight to allow conjugation to take place. These conjugates are hereafter described as PCA1-GOx and PCA2-GOx. They were stored in the fridge until required. As a control, a non-specific antibody-enzyme conjugate (comprising a rabbit antibody that does not bind to wine pigments but to a completely un-related antigen) was prepared by essentially the same method. This reagent is hereafter described as PCA(ns)-GOx.

Since chemical conjugation of enzyme can result in a partial loss in activity, it was necessary to determine the enzyme activity per unit volume for each of the conjugates so that exact equivalence of each could be added in the bleaching experiments. This was done using a colour-generating substrate system. A series of dilutions of each conjugate and of unconjugated GOx was made in b 0.1M phosphate buffer pH 6.5. 100 $\mu$l of each dilution was dispensed into the wells of a microtitre plate. Then 100 $\mu$l of substrate solution was added to each well. The Substrate solution was 50 mM glucose; 10 $\mu$g/ml horse radish peroxidase enzyme (Sigma), 10 $\mu$g/ml tetramethylbenzadine (Sigma); made up in 0.1M phosphate pH 6.5. Colouration in the wells was determined after 3 minutes by reading the absorbance at 630 nm. The GOx activity of each conjugate was approximated by comparing the amount of colour it could generate with that generated by unconjugated GOx.

EXAMPLE 16

Bleaching of Wine Stain with Antibody-enzyme Conjugate

Cotton swatches (2 cm×2 cm squares) that had been stained with red wine were rinsed in "wash buffer" i.e. PBS pH 7.2+0.075% Co—Co 6.5 EO as a surfactant. 6 of these swatches (still wet with wash buffer) were added to each of 15 containers of 100 ml capacity. lml of protein reagent, diluted in wash buffer, was added to each of the 15 containers: containers 1–3 received a dilution of PCA1-GOx; containers 4–6 received a dilution of PCA2-GOx; containers 7–9 received a dilution of PCA(ns)-Gox; containers 10–12 received a dilution of (unconjugated) GOx, containers 13–15 received a reagent blank i.e. wash buffer only. The protein reagents had all been diluted to have the same GOx activity, as described in Example 15. Containers were then incubated for 10 minutes at ambient temperature. Then 8 ml of a glucose solution, made up in wash buffer was added to each container: containers 1,4,7,10,13 received a 1 mM glucose solution, containers 2,5,8,11,14 received a 10 mM solution of glucose, containers 3,6,9,12,15 received a 50 mM solution of glucose. After addition of glucose solution, the protein reagents were at a final concentration that was equivalent in GOx activity to approximately 60 ng/ml of unconjugated enzyme, for the antibody-enzyme conjugates, this corresponded to approximately 300–400 ng/ml of antibody protein. The containers were then incubated at 37° C. for 1 hour. The swatches were rinsed in distilled water and dried overnight at 37° C. Stain removal was measured by analysing the cotton swatches with a spectrophotometre (Color-eye 7000, Macbeth, New Windsor, N.Y., USA). Measurements were made relative to an untreated standard (i.e. a cotton swatch that had been stained with red wine but not even rinsed with wash buffer). All six swatches were individually analysed with the Macbeth instrument. Readings were taken from each side of each swatch and then the mean of these two readings was recorded. The instrument was set up to take readings of AE, ΔL, and $\Delta R_{460}$.

In Table 4 below, stain removal data are expressed as ΔE: mean ΔE-values are recorded as taken from the six ΔE readings from the six individual swatches in each container. From these data, units of stain removal above that obtained with wash buffer only were calculated, by substracting the ΔE-value for wash buffer only from the ΔE-value for protein+wash buffer. These values are recorded as ΔΔE in Table 4. This figure can be considered as a measure of the removal of residual stain (i.e. that not removed by the surfactant only) and therefore it is an index of the benefit that is attributable to the protein reagent: the higher the ΔΔE, the more effective the protein is at removing stain.

Stain removal above that obtained with wash buffer only was seen in all samples that contained GOx (whether or not the enzyme was conjugated to antibody). In all cases, increasing the concentration of glucose from 1 mM to 10 mM improved removal of residual stain (i.e. increased ΔΔE) significantly. However, a further increase to 50 mM glucose did not produce a further increase in removal of residual stain, except in the case of (untargeted) GOx. In general, targeting the enzyme to stain by conjugating it to stain-binding antibody, improved the removal of residual stain. For example, when lOmM glucose was used, the targeted enzyme (i.e. that linked to PCA1 or PCA2) gave a 4-fold higher ΔΔE-value than the same amount of untargeted enzyme (i.e. either no antibody or non-specific antibody). See Table 4.

TABLE 4

Bleaching of wine stain from cotton fabric.

| Treatment* | | | Stain removal | Stain removal above "wash buffer" only |
|---|---|---|---|---|
| Container | Protein | Glucose | (ΔE) | (ΔΔE). |
| 1 | PCA1-GOx | 1 mM | 16.4 | 2.0 |
| 2 | PCA1-GOx | 10 mM | 19.2 | 4.8 |
| 3 | PCA1-GOx | 50 mM | 19.0 | 4.4 |
| 4 | PCA2-GOx | 1 mM | 15.8 | 1.4 |
| 5 | PCA2-GOx | 10 mM | 19.1 | 4.7 |
| 6 | PCA2-GOx | 50 mM | 18.5 | 3.9 |
| 7 | PCA (ns)-GO | 1 mM | 14.9 | 0.5 |
| 8 | PCA (ns)-GO | 10 mM | 15.7 | 1.3 |
| 9 | PCA (ns)-GO | 50 mM | 15.6 | 1.0 |
| 10 | GOx | 1 mM | 14.6 | 0.2 |
| 11 | GOx | 10 mM | 15.5 | 1.1 |
| 12 | GOx | 50 mM | 16.4 | 1.8 |
| 13 | None | 1 mM | 14.4 | — |
| 14 | None | 10 mM | 14.4 | — |
| 15 | None | 50 mM | 14.6 | — |

*Each of the above were applied in "wash buffer" i.e. phosphate buffered saline pH 7.2 containing Co-Co 6.5 EO as a surfactant.

Table 5 below records the spread of the data collected. For treatments at 10 mM glucose, the ΔE, ΔL, and $\Delta R_{460}$ readings are recorded for all six swatches.

TABLE 5

Repeat values for bleaching to wine stain from cotton fabric

| Treatment* | ΔE | ΔL | $\Delta R_{460}$ |
|---|---|---|---|
| PCA1-GOx | 19.3 | 13.3 | 17.3 |
| (Container 2) | 18.7 | 12.0 | 14.8 |
| | 19.8 | 13.9 | 17.8 |
| | 18.6 | 12.1 | 15.1 |
| | 18.6 | 12.0 | 15.0 |
| | 20.3 | 14.6 | 19.3 |

TABLE 5-continued

Repeat values for bleaching to wine stain from cotton fabric

| Treatment* | ΔE | ΔL | $\Delta R_{460}$ |
|---|---|---|---|
| PCA2-GOx | 18.5 | 12.2 | 15.9 |
| (Container 5) | 19.1 | 13.1 | 17.1 |
| | 18.8 | 12.6 | 16.3 |
| | 19.5 | 13.6 | 17.7 |
| | 19.0 | 13.0 | 17.1 |
| | 19.7 | 13.9 | 18.5 |
| PCA (ns) GOx | 15.4 | 7.9 | 10.9 |
| (Container 8) | 15.9 | 9.0 | 12.2 |
| | 15.8 | 8.5 | 11.4 |
| | 16.7 | 10.1 | 13.8 |
| | 15.2 | 7.4 | 9.1 |
| | 15.3 | 7.7 | 9.7 |
| GOx | 15.8 | 8.9 | n.d. |
| (Container 11) | 15.1 | 7.5 | n.d. |
| | 15.4 | 7.8 | n.d. |
| | 16.1 | 9.0 | n.d. |
| | 15.7 | 8.4 | 11.1 |
| | 15.0 | 7.3 | 10.1 |
| Reagent blank | 14.2 | 5.8 | 9.3 |
| (Container 14) | 15.0 | 7.5 | 11.6 |
| | 14.0 | 5.2 | 8.2 |
| | 14.5 | 6.7 | 10.4 |
| | 14.5 | 6.5 | 10.1 |
| | 14.1 | 5.8 | 9.4 |

*Each of the above were applied in "wash buffer" (i.e. phosphate buffered saline pH 7.2, containing 0.075% Co-Co 6.5 EO as a surfactant) and 10 mM glucose.
[n.d. = not determined].

Table 5 shows that it does not matter whether ΔE, ΔL, or $\Delta R_{460}$readings are used as a measure of stain removal: in all cases targeted enzyme (i.e. PCA1-GOx or PCA2-GOx) shows an increased stain removal over untargeted enzyme (i.e. PCA(ns)-GOx or GOx only). Furthermore, the six repeat values for each treatment are very similar and therefore there is a high degree of confidence that targeted enzyme really does improve stain removal.

EXAMPLE 17

Treating Dyed Cotton with Antibody-enzyme Conjugate

Fabric dyed with sulphur green or sulphol orange were used in these experiments because these dyes are known to be sensitive to bleach. The aim of these experiments was to determine if the wine-binding antibodies showed any cross-reactivity to the dye molecules, that could result in targeting the enzyme to the dye and therefore to its bleaching. (Bleaching is usually referred to as "fading" for dyes).

Dyed cloth was washed in PBS+0.075% Coco 6.5 E.O before incubation with either antibody-enzyme conjugate, free GOx or wash buffer only. Glucose was used at 10 mM throughout and incubation was for 1 hour at 37° C. In all other respects, the procedure was as described in Example 16.

Results of these experiments showed that dye fade with antibody targeted oxidase was not significantly increased over untargeted oxidase. See Tables 6a and 6b below. Therefore, the antibodies raised to wine show little or no cross-reactivity with the dye molecules. Furthermore, the destain to dye-fade ratio at 10 mM glucose is approximately 40. [Compare data in Table 4 with data in Table 6]. This means that the antibody-enzyme conjugate used together with 10 mM glucose shows a very high potential for removing stains such as red wine without damaging dyes on fabric.

TABLE 6a

Dye fade on Sulphol orange

| Treatment † | Dye fade (ΔE) | Dye fade above "wash buffer" only. (ΔΔE) |
|---|---|---|
| PCA1-GOx | 2.5 | 0.1 |
| PCA2-GOx | 2.3 | −0.1 |
| PCA (ns) -GOx | 2.6 | 0.2 |
| GOx | 2.4 | 0.0 |
| None | 2.4 | — |

TABLE 6b

Dye fade on Sulphur green 6

| Treatment † | Dye fade (ΔE) | Dye fade above "wash buffer" only. (ΔΔE) |
|---|---|---|
| PCA1-GOx | 0.96 | −0.04 |
| PCA2-GOx | 1.2 | 0.2 |
| PCA (ns) -GOx | 1.2 | 0.2 |
| GOx | 1.5 | 0.5 |
| None | 1.0 | — |

†Each of the above were applied in "wash buffer" (i.e. phosphate buffered saline pH 7.2, containing 0.075% Co-Co 6.5 EO as a surfactant) and 10 mM glucose.

What is claimed is:

1. A bleaching enzyme comprising an enzyme part capable of generating a bleaching chemical which is coupled to a peptide having a binding affinity for stains present on fabrics.

2. Enzyme according to claim 1, wherein the enzyme part is an oxidase and the bleaching chemical is hydrogen peroxide.

3. Enzyme according to claim 2, wherein the oxidase is selected from the group consisting of glucose oxidase, galactose oxidase and alcohol oxidase.

4. Enzyme according to claim 1, wherein the enzyme part is a haloperoxidase and the bleaching chemical is hypohalite.

5. Enzyme according to claim 1, wherein the enzyme part is a chloroperoxidase and the bleaching chemical is hypochlorite.

6. Enzyme according to claim 5, wherein the chloroperoxidase is a Vanadium chloroperoxidase.

7. Enzyme according to claim 6, wherein the Vanadium chloroperoxidase is *Curvularia inaegualis* chloroperoxidase.

8. Enzyme according to claim 1, where the enzyme part is a laccase or a peroxidase and the bleaching chemical is derived from an enhancer molecule that has reacted with the enzyme.

9. Enzyme according to claim 1, wherein the peptide has a binding affinity for porphyrin derived structures, tannins, polyphenols, carotenoid, anthocuanins, maillard reaction products.

10. Enzyme according to claim 1 wherein the fabric is cotton, polyester, or polyester/cotton fabric.

11. Enzyme according to claim 1, wherein the binding affinity has a chemical equilibrium constant $K_d$ of less than $10^{-4}$ M.

12. Enzyme according to claim 11, wherein the chemical equilibrium constant $K_d$ is less than $10^{-7}$ M.

13. Enzymatic bleaching composition comprising one or more surfactants and a bleaching enzyme according to claim 1.

14. Enzymatic bleaching composition comprising one or more surfactants, a bleaching enzyme according to claim 1 producing hydrogen peroxide and an activator which generates peracetic acid.

15. Enzymatic bleaching composition comprising one or more surfactants, a bleaching enzyme according to claim 1 producing hydrogen peroxide and a transition metal catalyst.

16. Process for bleaching stains present on fabrics, wherein stained fabrics are contacted with a solution comprising the bleaching enzyme according to claim 1.

17. Process for bleaching stains present on fabrics, wherein stained fabrics are contacted with an enzymatic bleaching composition according to claim 16.

* * * * *